United States Patent
Eckert et al.

(10) Patent No.: US 9,568,402 B2
(45) Date of Patent: Feb. 14, 2017

(54) PROCESSOR FOR PROCESSING HISTOLOGICAL SAMPLES

(71) Applicant: Leica Biosystems Nussloch GmbH, Nussloch (DE)

(72) Inventors: Ralf Eckert, Schriesheim (DE); Markus Berberich, Heidelberg (DE); Hermann Ulbrich, Bad Schoenborn (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 0 days.

(21) Appl. No.: 14/138,080

(22) Filed: Dec. 22, 2013

(65) Prior Publication Data

US 2014/0186883 A1 Jul. 3, 2014

(30) Foreign Application Priority Data

Dec. 28, 2012 (DE) .................... 20 2012 105 095 U
Mar. 15, 2013 (DE) ........................ 10 2013 204 645

(51) Int. Cl.
- *A61B 10/00* (2006.01)
- *G01N 1/31* (2006.01)
- *G01N 1/30* (2006.01)
- *G01N 1/28* (2006.01)

(52) U.S. Cl.
CPC ....... *G01N 1/31* (2013.01); *G01N 1/28* (2013.01); *G01N 1/30* (2013.01); *G01N 2001/305* (2013.01); *G01N 2001/315* (2013.01)

(58) Field of Classification Search
CPC ........................................................ G01N 1/36
See application file for complete search history.

(56) References Cited

U.S. PATENT DOCUMENTS

| | | | |
|---|---|---|---|
| 5,817,032 A * | 10/1998 | Williamson, IV | A61B 10/0096 422/536 |
| 2005/0226770 A1 | 10/2005 | Allen et al. | |
| 2006/0085140 A1 | 4/2006 | Feingold et al. | |
| 2008/0089808 A1 | 4/2008 | Shah | |
| 2010/0086964 A1* | 4/2010 | Walter et al. | 435/40.52 |
| 2010/0167334 A1* | 7/2010 | Williamson, IV | G06F 19/366 435/29 |

FOREIGN PATENT DOCUMENTS

| | | |
|---|---|---|
| DE | 19647662 | 3/1998 |
| DE | 10052832 | 4/2002 |
| DE | 10393978 | 12/2005 |
| DE | 102005057201 | 6/2007 |
| DE | 102007008713 | 8/2008 |
| DE | 102007044116 | 4/2009 |
| DE | 102008039861 | 3/2010 |
| DE | 102008039875 | 3/2010 |
| DE | 102008054066 | 5/2010 |
| DE | 102008054071 | 5/2010 |

(Continued)

OTHER PUBLICATIONS

Leica Peloris and Leica Peloris II; 2011.
Leica ASP300 S Operating Manual; Jan. 2008.

*Primary Examiner* — Jyoti Nagpaul
(74) *Attorney, Agent, or Firm* — Hodgson Russ LLP

(57) ABSTRACT

The disclosure relates to a processor for processing histological samples. The processor comprises an inlet for insertion of a closed fixing container having the samples present therein.

19 Claims, 2 Drawing Sheets

(56) References Cited

FOREIGN PATENT DOCUMENTS

| | | |
|---|---|---|
| DE | 102008056584 | 5/2010 |
| DE | 102009015596 | 10/2010 |
| DE | 102009025574 | 12/2010 |
| DE | 102009038481 | 2/2011 |
| DE | 202010012891 | 2/2011 |
| DE | 102011003366 | 8/2012 |
| DE | 102011003369 | 8/2012 |
| DE | 202012105095 | 1/2013 |
| DE | 202013103590 | 6/2014 |
| GB | 2487626 A | 1/2012 |
| WO | 9323732 A1 | 11/1993 |

\* cited by examiner

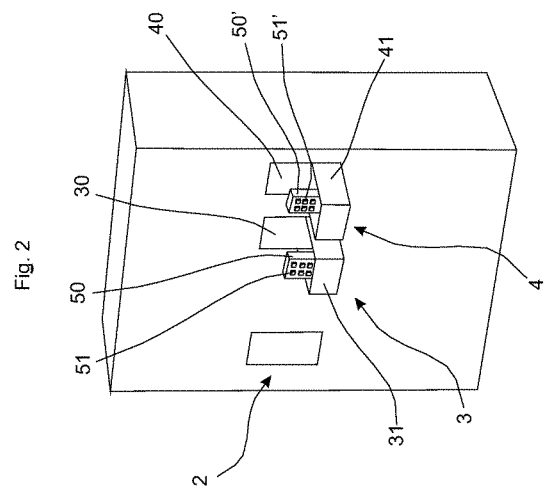
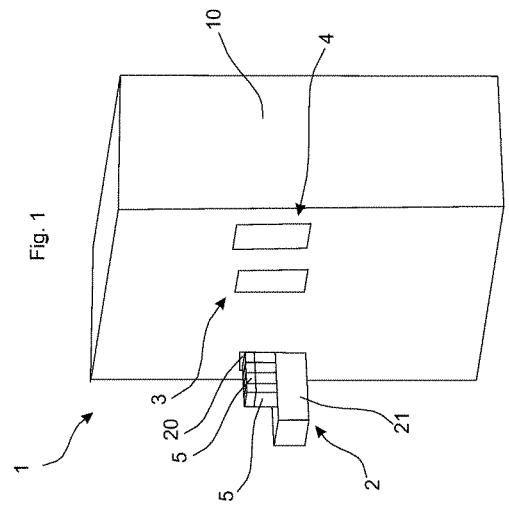

Fig. 3

PROCESSOR FOR PROCESSING HISTOLOGICAL SAMPLES

CROSS REFERENCE TO RELATED APPLICATIONS

This application claims priority of German utility model no. 20 2012 105 095.1 filed Dec. 28, 2012 and German patent application number 10 2013 204 645.6 filed Mar. 15, 2013, the entire disclosures of which are incorporated by reference herein.

FIELD OF THE DISCLOSURE

The present disclosure relates to a processor for processing histological samples. The present disclosure furthermore relates to a holding device. The present disclosure moreover relates to a method for processing a histological sample.

BACKGROUND OF THE DISCLOSURE

The purpose of treating a histological sample, for example one taken from a patient, is to bring that sample into a state that permits sectioning into thin layers using a microtome. This treatment takes place in multiple processing stations. Sectionability can be enabled, for example, by the fact that in multiple successive processing steps, a mechanically stabilizing medium is introduced (infiltrated) into the tissue. Alternatively, the tissue can also be frozen.

A plurality of processing stations for processing histological samples are already known from the existing art. For example, processing stations in the form of trimming stations, fixing stations, dehydration stations, clearing stations, infiltration stations, embedding stations, or microtomes (sectioning stations) are known in a wide variety of embodiments. Dehydration, clearing, and infiltration can occur in different treatment stations of a single device, which is referred to hereinafter as a "processor."

In a trimming station, the tissue (removed, for example, from the patient) is cut into individual samples. The samples are usually placed into cassettes and transported to a fixing station. Fixing of the samples is necessary because the supply of oxygen to the cells is suppressed after removal of the tissue from the patient, which results in cell death. Firstly a swelling of the cells can be observed; protein denaturing also occurs, and autolysis with subsequent bacterial digestion. In order to counteract this damage, the samples that have been removed are fixed in the fixing station with a fixative, for example formalin.

After treatment in the fixing station, dehydration of the samples occurs in a dehydration station. Dehydration of the samples is necessary in order to enable the subsequent process of infiltration and embedding.

Because the fixative (in particular formalin) is usually an aqueous medium, whereas the infiltration or embedding medium to be used (in particular paraffin) is usually a medium not miscible with water, the samples must be dehydrated before further treatment of the samples in the dehydration station. Dehydration of the samples is accomplished with the aid of a dehydration agent, for example ethanol.

Before the samples are transferred to the infiltration station, they are also cleared. Clearing is necessary because the alcohol in the tissue of the sample is not miscible with paraffin. The alcohol must therefore be removed from the tissue before infiltration, and replaced with a reagent miscible with paraffin, for example xylene.

After treatment of the sample in the clearing station, it is brought to an infiltration station. In the infiltration station an infiltration agent, which usually corresponds to the embedding agent used later, is introduced into cavities of the sample until it is saturated. Introduction of the infiltration agent allows the samples to be mechanically stabilized.

Following treatment of the sample in the infiltration station, it is processed in the embedding station. In the embedding station the histological sample is embedded into an embedding agent such as paraffin or wax. In practice, the term "embedding" is used in two ways. On the one hand it is a synonym for "infiltration," which occurs in the aforementioned infiltration station; on the other hand, it has the same meaning as "embedding" or "block embedding," which occurs in the embedding station.

For embedding, the samples are placed into molds and the mold is filled with the embedding agent. The histological sample is then cooled so that the embedding agent can harden. To cool the histological samples they are, for example, placed onto a cooling plate of the embedding station. The result is to create an embedded block in which the sample is immobilized in stationary fashion. After hardening of the embedding agent, the sample can be sectioned with the microtome into individual thin sample sections, which in a subsequent step can be stained and investigated with a microscope.

To ensure that the sectioning operation with the microtome can be carried out precisely, it is necessary for the embedded block to remain in a hard state. In practice, a laboratory worker transports the cassettes individually from the embedding station to the microtome. Alternatively, it is known that the laboratory worker does not transport the cassettes individually, but instead places them from the cooling plate of the embedding station into a transport basket. The transport basket is then transported to a microtome, with which the samples present in the transport basket are processed.

In embodiments known from the existing art, the fixed sample is removed from the fixing container by the user and put into the processor. In the processor, dehydration, clearing, and infiltration of the sample occur in the corresponding aforementioned treatment stations of the processor. The infiltrated sample is then delivered to an embedding station arranged physically separately from the processor.

The known embodiment is disadvantageous in that the fixing container must be manually opened in the laboratory in order to remove the samples. In addition, the user must manually take the samples out of the fixing container and introduce them into the processor. The result is that the user must perform a number of time-consuming working steps.

The object of the invention is therefore to make available a processor that decreases the number of time-consuming working steps carried out by the user of the processor.

SUMMARY OF THE DISCLOSURE

The object is achieved by a processor for processing histological samples that comprises an inlet for inserting a fixing container having the samples present therein. The fixing container can be closed and can contain a plurality of samples that are wetted by a fixative, for example formalin, present in the fixing container. The processor can comprise a single inlet.

Thanks to the provision of an inlet for the fixing container, the user simply needs to insert the fixing container into the processor. This means that the processor automatically carries out at least removal of the at least one sample from the fixing container, thereby eliminating this working step for the user. In addition, the processor can be embodied in such a way that it automatically opens the closed fixing container in order to remove the samples from the fixing container, so that this working step is also eliminated for the user. This can be implemented by the fact that the fixing container comprises a slot that is closed off by a flap. The flap is opened in order to remove the samples from the fixing container, which can be accomplished e.g. by a handling apparatus arranged in the processor and explained below. The result is to prevent fixative vapors from propagating in the laboratory after the fixing container is opened.

In addition, provision can be made to arrange the samples in cassettes that are arranged in a releasably fastened manner in a holding device. The holding device can be removed from the fixing container.

In an embodiment of the invention, processing of the samples can occur in multiple treatment stations that are arranged in the processor, and in an embedding station downstream from the treatment stations. For purposes of the inventions, the treatment stations are all stations in which the samples are treated after removal from the fixing container and before delivery into the embedding station. The treatment stations can in particular be the dehydration station, the clearing station, or the infiltration station. Each of the treatment stations can comprise a reagent container that is filled with a reagent and into which the samples are introduced.

In an alternative embodiment, processing of the sample can be accomplished by, in particular, a single treatment station and an embedding station downstream from the treatment station. The treatment station comprises a single sample receiving container that is fluidically connected to at least one reagent container and/or is arranged physically separately therefrom. In the sample receiving container, all treatment operations subsequent to the fixing operation and preceding the embedding operation can be accomplished.

The sample receiving container can be connected at least to a dehydration agent container, to a clearing agent container, and/or to an infiltration agent container. For treatment of the samples present in the sample receiving container the reagents are delivered successively, in particular only, thereinto. In this embodiment, transportation of the sample into the different reagent containers is not necessary, thereby achieving a simple and compact configuration for the processor.

In a particular embodiment, an embedding station can be integrated into the processor. A further working step for the user is thereby eliminated, since he or she no longer needs to transport the infiltrated samples from the processor to the embedding station. Moreover, the processor is of more compact configuration compared with embodiments in which the processor and the embedding station are devices arranged physically separately from one another; this is advantageous because of the shortage of space in laboratories. The processor can comprise a housing that encloses both the embedding station and the at least one treatment station of the processor.

After an insertion of the fixing container into the processor, the latter is located directly in an interior space of the processor. In this, the fixing container can be opened for removal of the samples. The processor can furthermore comprise an aspiration device by means of which the fixative vapors are aspirated. The result is that propagation of fixative vapors in the laboratory can be suppressed in simple fashion.

The inlet can comprise a pull-out inlet drawer for insertion of at least one fixing container. The provision of the inlet drawer offers the advantage that multiple fixing containers can be introduced simultaneously into the processor, which once again represents a simplification for the user. With the inlet drawer in a pulled-out state, the fixing containers can be inserted thereinto. With the inlet drawer in a pulled-in state, the fixing containers are located in the interior space of the processor.

In a particular embodiment, the processor can comprise a separator apparatus. The separator apparatus can physically separate samples to be embedded from samples that are not to be embedded. The background here is that in practice, for a wide variety of reasons such as inopportune sectioning or because of their nature, individual samples cannot be processed, or at least cannot be completely processed, by means of the processor, in particular cannot be embedded. The separator apparatus recognizes these samples that are not to be embedded, and separates them from the remaining samples that are to be embedded. Separation of the samples can occur before they are conveyed into the embedding station. For example, the separator apparatus can comprise a sensor device, in particular an optical sensor. Based on the values supplied by the sensor apparatus, a determination can be made as to whether or not the sample is to be embedded. Provision of the separator apparatus has the advantage that the user of the processor does not need to examine all the samples as to whether or not they are to be embedded.

The processor can comprise two outlets, a first outlet serving to discharge samples that are that have been separated by the separator apparatus and are not to be embedded. A second outlet serves to discharge embedded samples. This means that the rejected, unembedded samples can be easily identified and removed by the user.

In a particular embodiment, the processor can comprise a handling apparatus that removes the samples, or the holding device having the cassettes and samples, from the fixing container or delivers them to the sample receiving container or to the reagent container. In particular, the same sample handling apparatus can carry out a step of transporting the samples from one treatment station of the processor to another treatment station of the processor. Alternatively or additionally, the same handling apparatus can carry out a transport step from a treatment station of the processor to the embedding station of the processor. A handling apparatus embodied in this fashion offers the advantage that it is of simple configuration and at the same time ensures that transport between the treatment stations, and/or between a treatment station and the embedding station, occurs without intervention by the user.

The processor can comprise at least one communication means for communicating with another communication means associated with the sample. In particular, the communication means can be provided on the handling apparatus. The other communication means associated with the sample can be mounted on the holding device on which the samples are secured. At least one of the communication means can comprise a reading means and/or writing means. The communication means can be an RFID chip. Furthermore, at least one communication means can comprise a memory in which sample-specific and/or process-specific data are stored. The other communication means mounted on the holding device can in particular contain sample-specific and/or process-specific data.

The data can be, for example, data relating to the point in time at which the samples were introduced into the fixing container. Alternatively or additionally, the data can relate to the length of time during which the samples are wetted with the reagents. Further data can of course also be stored in the memory. A control apparatus can control the handling apparatus, and thus the processing of the samples, based inter alia on the aforementioned data.

For example, provision can be made that different process steps can be selected by way of the communication means so that multiple samples can be treated concurrently in different treatment stations. It is also possible to modify, by way of the communication means, the sequence of the samples in the context of treatment, for example so that urgent samples can be preferentially treated and/or in order to ensure optimum occupancy of the individual treatment stations.

The handling apparatus can be embodied to remove the holding device from the inserted fixing container. The holding device can comprise a holding frame that carries at least one cassette, preferably a plurality of cassettes, at least one sample being arranged in the cassette. The handling apparatus can consequently remove a plurality of samples, secured on the holding device and thus on the holding frame, simultaneously from the fixing container. The outlay for removing the sample from the fixing container is thereby reduced, or does not exist, for the user.

The processor can furthermore be embodied so that the at least one sample remains in the same cassette during at least one treatment step and during an embedding step different from the treatment step. This eliminates the working step, known from the existing art, in which the samples are removed by the user from the cassette and are manually put into a casting mold for the embedding operation. The treatment step can be, for example, the dehydration, clearing, and/or infiltration operation.

In a particular embodiment, a, in particular a single, operating element can be provided for operating the processor, in particular together with the embedding station. Alternatively or additionally, a, in particular a single, control software program can be provided for controlling the processor, in particular together with the embedding station. Simple operation and/or control of the processor is thereby possible. The processor can comprise a, in particular a single, interface for an electronic data connection. The processor can thereby be connected at a defined interface to other data devices.

A further object of the invention is that of efficiently configuring the removal of the samples from the fixing container and/or the processing of the samples in the processor. This object is achieved by a holding device that is used in the processor described above. The holding device, in particular a holding frame of the holding device, carries at least one, in particular a plurality of cassettes, in each of which at least one sample is arranged. A holding device embodied in this fashion offers the advantage that a plurality of samples are simultaneously transported or processed. A holding device of this kind can also be used in the context of the processing of histological samples independently of the special utilization in the above-described processor, and in that regard is in fact a subject of an independent inventive idea.

Another object of the invention is that of describing a method for processing a histological sample, with which method the working steps to be effected by the user are reduced. The object is achieved by a method for processing at least one histological sample, which method utilizes the processor described above.

In a particular embodiment, the cassettes can remain in the holding device during at least one treatment step and/or embedding step and/or transport step. This ensures that treatment and/or embedding and/or transport of a plurality of cassettes, and thus samples, is possible simultaneously The position of a cassette, in particular within the interior space of the processor, can remain unchanged during the at least one treatment step and/or embedding step. This is possible in particular in the processor embodiment in which treatment of the samples occurs only in the sample receiving container. In particular, the holding device and/or at least one cassette can be conveyed out of the fixing container into the sample receiving container. A treatment agent, such as a dehydration agent, can then be delivered into the sample receiving container. The dehydration agent can of course also be delivered into the sample receiving container before introduction of the holding device and/or of the at least one cassette. After treatment of the samples by means of the dehydration agent, the latter is drained off and a new treatment agent, for example the clearing agent, is introduced into the container. Delivery and drainage of the respective treatment agents occurs until the samples have been processed with all the necessary treatment agents.

In a particular embodiment, the position of the holding device and/or of the cassette, in particular within the interior space of the processor, can be modified only upon transportation of the cassette from the fixing container to the treatment station and/or upon transportation of the holding device and/or of the cassette from the treatment station to the embedding station. A simple method and a processor of simple configuration are achieved as a result.

BRIEF DESCRIPTION OF THE DRAWINGS

The subject matter of the invention is schematically depicted in the drawings and will be described below with reference to the illustrations, identical or identically functioning elements usually being provided with the same reference characters. In the drawings:

FIG. 1 is a perspective depiction of the processor according to the present invention with the inlet drawer pulled out, FIG. 2 is a perspective depiction of the processor according to the present invention with the outlet drawers pulled out, FIG. 3 is a sectioned view of the processor from the front.

DETAILED DESCRIPTION OF THE DISCLOSURE

Processor 1 depicted in FIG. 1 comprises a housing 10, an inlet 2, and a first and a second outlet 3, 4. Inlet 2 comprises an inlet opening 20 and a pulled-out inlet drawer 21. Drawer 21 comprises receptacles (not depicted) for receiving fixing containers 5. Provided in fixing containers 5 is a first and second holding frame 50, 50' of a first and a second holding device, which carries a plurality of cassettes 51, 51' in which at least one sample is arranged.

As is evident from FIG. 2, first outlet 3 comprises a first outlet opening 30 and a first outlet drawer 31, and second outlet 4 comprises a second outlet opening 40 and a second outlet drawer 41. The two outlet drawers 31, 41 are pulled out, and each comprise receptacles (not depicted) for receiving holding frames 50, 50'. First outlet drawer 31 serves to discharge first cassettes 51 mounted on a first holding frame 50. First cassettes 51 contain samples that have not been embedded in the embedding station integrated into processor 1. Second outlet drawer 41 serves to discharge second cassettes 51' mounted on a second holding frame 50'. Second cassettes 51' contain samples that have been embedded in the embedding station of processor 1.

Figure 3:
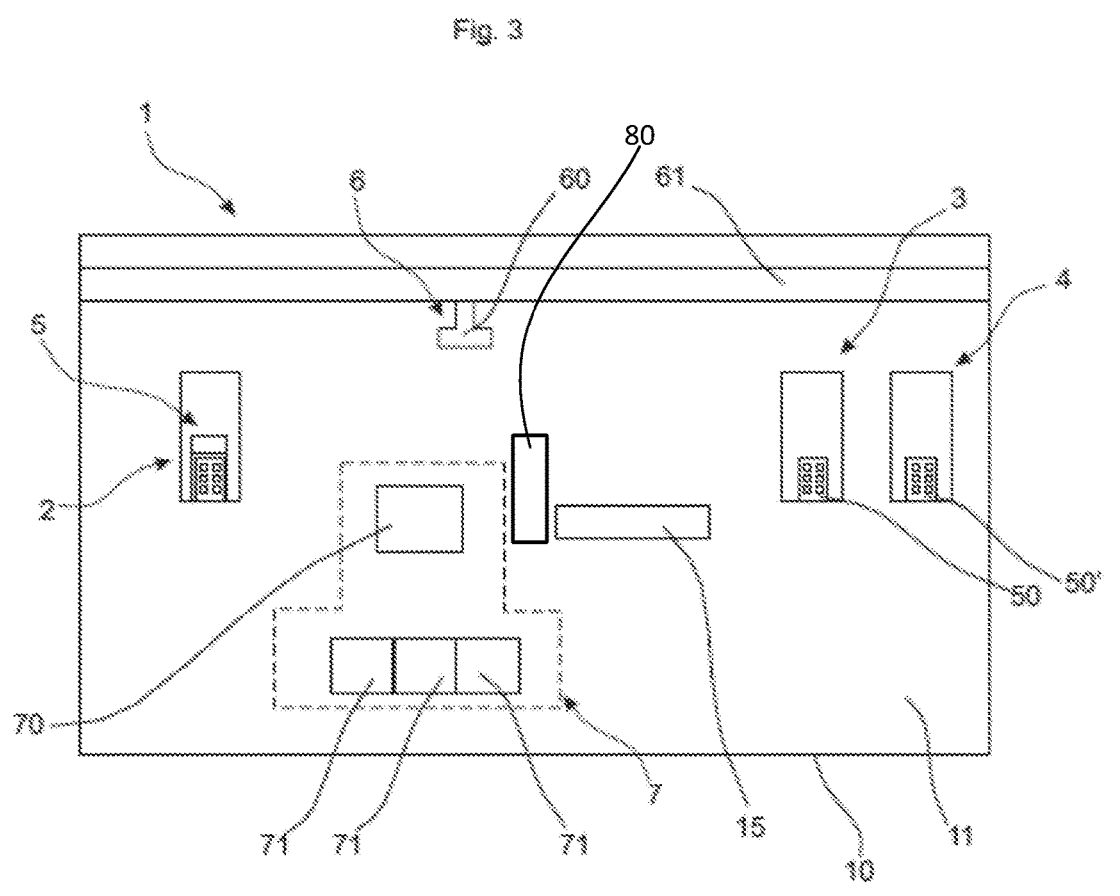

FIG. 3 is a schematic sectioned view of processor 1 from the front. FIG. 3 shows in particular some of the components present in an interior space 11 of processor 1.

Processor 1 comprises a handling apparatus 6 that can move in both a vertical and a horizontal direction in interior space 11 of processor 1 defined by housing 10. The motion of the handling apparatus can be guided by rails 61 that guide the motion of handling apparatus 6 in a horizontal direction, only one rail 61 being depicted in FIG. 3. Handling apparatus 6 comprises a gripper 60 that can be brought into a releasable connection with holding frame 50, 50'.

Processor 1 furthermore comprises a single treatment station 7 having a sample receiving container 70 for treating the samples. Sample receiving container 70 is connected via lines (not depicted) to a plurality of reagent containers 71 of treatment station 7. A dehydration agent, clearing agent, or infiltration agent can be contained in reagent container 71.

Processor 1 furthermore comprises a separator apparatus 80 and an embedding station 15 that are downstream from treatment station 7. The separator apparatus 80 serves to identify the samples that are not to be embedded in embedding station 15. The separator apparatus 80 is furthermore arranged in a transport path of handling apparatus 6 between treatment station 7 and 20 embedding station 15.

The manner of operation of processor 1 will be explained below. After fixing containers 5 are introduced into inlet drawer 21, and after inlet drawer 21 is brought into the pulled-in state, gripper 60 of handling apparatus 6 pulls holding frame 50, 50' out of fixing container 5. This is possible because a slot, shaped oppositely to gripper 60, is provided in a cover of fixing container 5, through which slot gripper 60 can penetrate into fixing container 5 in order to remove holding frame 50, 50' therefrom.

Handling apparatus 6 transports holding frame 50, 50' into sample receiving container 70. In the latter, holding frame 50, 50', and thus the samples secured on the holding frame, are treated successively with multiple reagents provided in reagent containers 13. Subsequently thereto, handling apparatus 6 conveys holding frames 50, 50' to the separator apparatus 80, which determines whether or not the samples secured on holding frame 50, 50' will be embedded.

Handling apparatus 6 transports the samples that are to be embedded to embedding station 15, in which embedding thereof occurs. After embedding the samples are completely processed, and are transported via handling apparatus 6 to second outlet 4. Conversely, handling apparatus 6 transports the samples that are not to be embedded directly from the separator apparatus 80 to first outlet 3.

Although the present invention has been described with respect to one or more particular embodiments, it will be understood that other embodiments of the present invention may be made without departing from the spirit and scope of the present invention.

PARTS LIST

1 Processor
2 Inlet
3 First outlet
4 Second outlet
5 Fixing container
6 Handling apparatus
7 Treatment station
10 Housing
11 Interior space of processor
15 Embedding station
20 Inlet opening
21 Inlet drawer
30 First outlet opening
31 First outlet drawer
40 Second outlet opening
41 Second outlet drawer
50 First holding frame
50' Second holding frame
51 First cassette
51' Second cassette
60 Gripper
61 Rail
70 Sample receiving container
71 Reagent container
80 Separator apparatus

What is claimed is:

1. A processor (1) for processing histological samples, comprising:
    an inlet (2) configured to receive a closed fixing container (5), the closed fixing container (5) configured to hold a fixative and the histological samples;
    an embedding station integrated into the processor (1);
    a separator apparatus configured to physically separate histological samples in the processor (1) to be embedded from histological samples in the processor (1) that are not to be embedded, wherein the separator apparatus is disposed in the processor (1) between a treatment station and the embedding station; and
    at least two outlets (3, 4), a first outlet (3) serving to discharge unembedded samples of the histological samples that have been separated by the separator apparatus, and a second outlet (4) serving to discharge embedded samples of the histological samples.

2. The processor (1) according to claim 1, wherein the closed fixing container (5) is arranged directly in an interior space (11) of the processor (1) after the closed fixing container (5) is inserted into the processor (1).

3. The processor (1) according to claim 1, wherein the inlet (2) comprises a pull-out inlet drawer (21) configured to receive the closed fixing container (5).

4. The processor (1) according to claim 1, further comprising a handling apparatus (6) configured to remove the histological samples from the closed fixing container (5) or configured to deliver the histological samples to a sample receiving container (70) or to a reagent container, wherein the handling apparatus (6) is disposed in the processor (1).

5. The processor (1) according to claim 4, wherein the sample handling apparatus (6) is configured to transport the histological samples from the treatment station of the processor (1) to another treatment station of the processor (1) and/or configured to transport from the treatment station of the processor (1) to the embedding station (15) of the processor (1).

6. The processor (1) according to claim 4, wherein the handling apparatus (6) is configured to remove from an inserted fixing container (5) a holding device that carries at least one cassette (51, 51') having at least one sample of the histological samples.

7. The processor (1) according to claim 1, further comprising a communication device configured to communicate with another communication device associated with a histological sample of the histological samples, the another communication device being mounted on a holding device on which the histological samples are secured.

8. The processor (1) according to claim 1, further comprising a single sample receiving container (70) in fluid communication with at least one reagent container (71).

9. The processor (1) according to claim 1, wherein the processor (1) is configured such that the sample remains in the same cassette (51, 51') during at least one treatment step and during an embedding step different from the treatment step.

10. The processor (1) according to claim 1, further comprising an operating element configured to operate the processor (1), together with the embedding station, and/or a control software program stored on non-transitory computer-readable medium configured to control the processor (1), with the embedding station.

11. The processor (1) according to claim 1, characterized by a single interface for an electronic data connection.

12. A holding device for use in a processor (1) according to claim 1, the holding device carrying at least one cassette (51, 51') in which at least one sample is arranged.

13. A method for processing at least one histological sample, comprising:
    providing a processor (1), the processor (1) including an inlet (2) configured to receive a closed fixing container (5), the closed fixing container (5) configured to hold a fixative and the at least one histological sample located in a cassette (51, 51');
    processing the at least one histological sample with the processor (1), wherein the processing includes an embedding step; and
    physically separating histological samples in the processor (1) to be embedded from histological samples in the processor (1) that are not to be embedded with a separator apparatus, wherein the separator apparatus is disposed in the processor (1) between a treatment station and an embedding station.

14. The method according to claim 13, wherein the cassette (51, 51') remains in a holding frame (50, 50') of the holding device, during at least one treatment step and/or transport step.

15. The method according to claim 13, wherein a position of the cassette (51, 51') relative to the holding device remains unchanged during at least one treatment step and/or the embedding step and/or transport step.

16. The method according to claim 13, wherein a position of the cassette (51, 51') within an interior space of the processor (1) remains unchanged during at least one treatment step and/or the embedding step.

17. The method according to claim 13, wherein a position of the cassette (51, 51') within an interior space of the processor (1), is changed only upon transportation of the cassette (51, 51') from the closed fixing container (5) to the treatment station and/or upon transportation of the cassette (51, 51') from the treatment station to the embedding station.

18. A processor (1) for processing histological samples, comprising:
    an inlet (2) configured to receive a closed fixing container (5), the closed fixing container (5) configured to hold a fixative and the histological samples;
    a handling apparatus (6) configured to remove the histological samples from the closed fixing container (5) or configured to deliver the histological samples to a sample receiving container (70) or to a reagent container, wherein the handling apparatus (6) is disposed in the processor (1);
    a separator apparatus configured to physically separate histological samples in the processor (1) to be embedded from histological samples in the processor (1) that are not to be embedded, wherein the separator apparatus is disposed in the processor (1) between a treatment station and an embedding station; and
    at least two outlets (3, 4), a first outlet (3) serving to discharge unembedded samples of the histological samples that have been separated by the separator apparatus, and a second outlet (4) serving to discharge embedded samples of the histological samples.

19. A method for processing at least one histological sample, comprising:
    providing a processor (1), the processor (1) including an inlet (2) configured to receive a closed fixing container (5), the closed fixing container (5) configured to hold a fixative and the at least one histological sample located in a cassette (51, 51'), and a handling apparatus (6) configured to remove the at least one histological sample from the closed fixing container (5) or configured to deliver the at least one histological sample to a sample receiving container (70) or to a reagent container,
    wherein the handling apparatus (6) is disposed in the processor (1);
    processing the at least one histological sample with the processor (1); and
    physically separating histological samples in the processor (1) to be embedded from histological samples in the processor (1) that are not to be embedded with a separator apparatus, wherein the separator apparatus is disposed in the processor (1) between a treatment station and an embedding station.

* * * * *